United States Patent
Belhadj et al.

(10) Patent No.: US 12,402,856 B2
(45) Date of Patent: Sep. 2, 2025

(54) ULTRASOUND IMAGING METHOD FOR MEASURING AN OBJECT

(71) Applicant: COMMISSARIAT A L'ENERGIE ATOMIQUE ET AUX ENERGIES ALTERNATIVES, Paris (FR)

(72) Inventors: Djallel Belhadj, Gif-sur-Yvette (FR); Sylvain Chatillon, Gif-sur-Yvette (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 18/977,422

(22) Filed: Dec. 11, 2024

(65) Prior Publication Data

US 2025/0195030 A1    Jun. 19, 2025

(30) Foreign Application Priority Data

Dec. 18, 2023 (FR) ..................... 2314348

(51) Int. Cl.
*A61B 8/08* (2006.01)
*A61B 8/00* (2006.01)

(52) U.S. Cl.
CPC .......... *A61B 8/0891* (2013.01); *A61B 8/4483* (2013.01); *A61B 8/54* (2013.01)

(58) Field of Classification Search
CPC .................................................. A61B 8/0891
See application file for complete search history.

(56) References Cited

U.S. PATENT DOCUMENTS

2021/0100523 A1* 4/2021 Jiang ............... A61B 8/488

FOREIGN PATENT DOCUMENTS

JP          5854072 B2    2/2016
WO    2016/057233 A1    4/2016

OTHER PUBLICATIONS

Gagan, et al., "Automated Segmentation of Common Carotid Artery in Ultrasound Images", in IEEE Access, vol. 10, pp. 58419-58430, 2022.
Savoia, et al., "A feasibility study of a PMUT-based wearable sensor for the automatic monitoring of carotid artery parameters", 2021 IEEE International Ultrasonics Symposium (IUS), 2021.
English translation of the Preliminary Search Report and Written Opinion on Patentability of the Invention issued in French Patent Application No. 2314348 dated Jul. 10, 2024.

* cited by examiner

*Primary Examiner* — Joel Lamprecht
*Assistant Examiner* — Nyrobi Celestine
(74) *Attorney, Agent, or Firm* — BakerHostetler

(57) ABSTRACT

A method for characterising an object using an ultrasound probe, the method including the following steps of: carrying out several iterations of the following steps of: i. transmitting an ultrasound field having an aperture with a given size; ii. measuring an echo of the ultrasound field following reflection on a zone of interest of an object to be imaged; iii. modifying, for each new iteration, the size of the aperture of the ultrasound field; recording, for at least one point of interest in the zone of interest, the associated time-of-flight on the measurement of the echo; determining, based on the time-of-flight measurements, a variation model of the times-of-flight as a function of the size of the aperture of the ultrasound field; extrapolating the time-of-flight of the point of interest for an aperture size tending towards 0 based on said model.

7 Claims, 6 Drawing Sheets

ULTRASOUND IMAGING METHOD FOR MEASURING AN OBJECT

CROSS-REFERENCE TO RELATED APPLICATION

This application claims priority to foreign French patent application No. FR 2314348, filed on Dec. 18, 2023, the disclosure of which is incorporated by reference in its entirety.

FIELD OF THE INVENTION

The invention relates to the field of ultrasound imaging, in particular medical imaging, and relates to a method for improving the precision of such measurements when they are carried out by means of an ultrasound probe having an aperture field of the transmitted ultrasound field that assumes a given size.

BACKGROUND

The invention notably applies to the imaging of blood vessels, for example, arteries, with a view to precisely determining the diameter of such vessels, but it is not limited to this application and is more generally aimed at improving measurement precision for ultrasound imaging of all types of objects in the medical field or in the field of non-destructive ultrasound inspecting.

In general, and particularly in the medical field, ultrasound imaging is a tool for precisely monitoring, sometimes in real time, certain anatomical objects, such as blood vessels. In particular, it allows the dimensions of these vessels to be located and measured. However, the precision of ultrasound measurements varies according to the type of equipment that is used.

The development of ultrasound-based technologies has resulted in compact monitoring systems offering a non-invasive solution. Fully automated portable real-time monitoring can provide both relevant information on daily life and data over longer durations in situations that are inaccessible in healthcare departments with fixed equipment.

However, portable ultrasound imaging devices are limited in terms of resources and energy consumption, which means that they must compromise in terms of the precision and the frequencies used, which in turn limits the usability of the gathered data. These limitations in terms of frequency and precision make early discovery of diseases less likely, and limit the progress and understanding of phenomena of interest, such as cardiovascular diseases in the medical field, for example. Conventionally, the existing solutions have tended to prioritise precision to the detriment of energy consumption, low cost and the simplicity of the algorithms.

Therefore, a general problem exists of improving the precision of ultrasound imaging systems without increasing their energy consumption or their cost, and without having to modify existing equipment.

In the field of medical imaging, several existing methods allow arteries to be detected and characterised. Notably, references [1] and [2] and patent application WO 2016/057233 can be cited.

All these methods have the disadvantage of suffering from limited measurement precision since in most cases they are based on an ultrasound acquisition method that uses a set of elements to generate an ultrasound field with an aperture whose size depends on the number of elements. The precision of the measurements depends on various parameters, in particular the frequency and the bandwidth of the signal. However, it also depends on the size of the active window of the probe, i.e., the total size of the set of active elements.

The smaller the active window, the higher the precision of the measurement in terms of resolution. However, an active window that is too small has the disadvantage of lowering the signal-to-noise ratio since the signal amplitude is lower. It is for this second reason that ultrasound probes are generally based on multi-element transducers that use several active elements to synthesise an ultrasound beam, in order to focus the beam by coherent summation of the amplitudes of the various elements.

SUMMARY OF THE INVENTION

The invention is based on an algorithmic solution that allows the resolution and the precision of the measurement to be improved without modifying the acquisition equipment. The method is based on carrying out several successive measurements by varying the number of active elements or the aperture size of the generated ultrasound field and then extrapolating the measurement that would have been obtained with an aperture close to zero based on the various acquired measurement points.

The aim of the invention is a method for characterising an object using an ultrasound probe, the method comprising the following steps of:
  carrying out several iterations of the following steps of:
    i. transmitting an ultrasound field having an aperture with a given size;
    ii. measuring an echo of the ultrasound field following reflection on a zone of interest of an object to be imaged;
    iii. modifying, for each new iteration, the size of the aperture of the ultrasound field;
  recording, for at least one point of interest in the zone of interest, the associated time-of-flight on the measurement of the echo;
  determining, based on said time-of-flight measurements, a variation model of the times-of-flight as a function of the size of the aperture of the ultrasound field;
  extrapolating the time-of-flight of the point of interest for an aperture size tending towards 0 based on said model.

According to a particular aspect of the invention, the ultrasound probe comprises a plurality of elements and the variation in the size of the aperture of the ultrasound field is obtained by varying the number of reception active elements.

According to a particular aspect of the invention, the number of reception active elements is a multiple of two.

According to a particular aspect of the invention, the number of transmission active elements is equal to the number of reception active elements or to the maximum number of elements included in the probe.

According to a particular aspect of the invention, the object to be imaged is a blood vessel and the point of interest is a point on a wall of the blood vessel.

According to a particular aspect of the invention, the method is applied for two points of interest corresponding to a first point on the distal wall of the blood vessel and a second point on the proximal wall of the blood vessel, diametrically opposite the first point, and the method further comprises estimating the diameter of the blood vessel based on the extrapolated times-of-flight of the two points.

A further aim of the invention is an ultrasound imaging device comprising an ultrasound probe and a processing unit configured to carry out the steps of the method according to the invention.

The invention thus allows measurement precision to be optimised without having to modify the ultrasound probe.

BRIEF DESCRIPTION OF THE DRAWINGS

Further features and advantages of the present invention will become more clearly apparent from reading the following description, with reference to the following appended drawings, in which:

FIG. 3b shows an ultrasound signal extracted from a column of the image of FIG. 3a;

DETAILED DESCRIPTION

The invention will now be described within the scope of application of medical imaging of a blood vessel, for example, an artery. Although the invention advantageously applies to this example, it is not limited to this specific case and more generally applies to any type of object to be imaged, particularly in the field of non-destructive inspecting and for any point of interest on an object to be precisely located.

Figure 1:
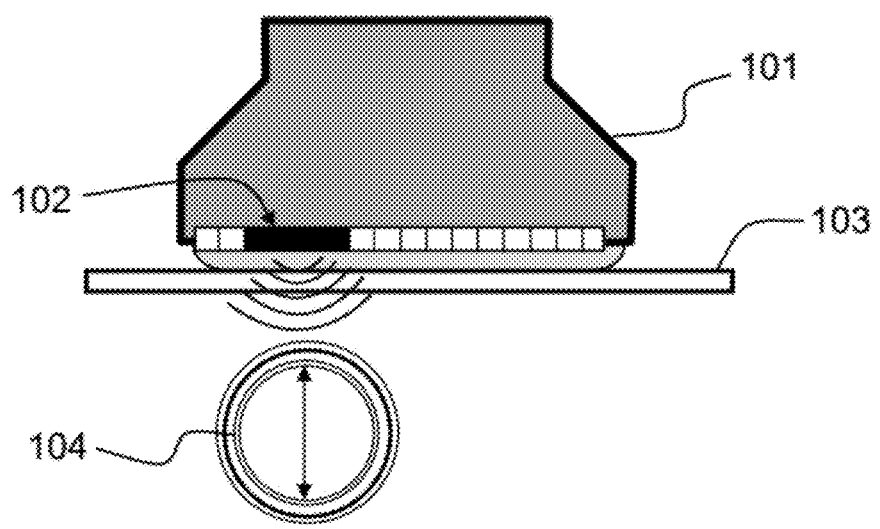
FIG. 1 shows a diagram of a multi-element ultrasound probe capable of carrying out an ultrasound signal acquisition sequence for imaging a blood vessel.

FIG. 1 schematically shows an example of a multi-element ultrasound probe capable of imaging an area of the human body using an ultrasound beam. In the example shown in FIG. 1, the area corresponds to a transverse plane of a blood vessel to be precisely located or whose diameter is to be precisely determined.

In the example shown in FIG. 1, the probe 101 is positioned in contact with the skin 103 so that the row of elements 102 is substantially located in a transverse plane of an artery 104 to be imaged. The probe 101 is not necessarily centred on the artery 104, the artery simply needs to be covered on transmission and on reception by the ultrasound beam generated by the probe in order to obtain a transverse impression of the artery.

In order to carry out an acquisition, the probe is positioned at a given point and a group of transmission elements is activated so as to generate an ultrasound field in a given direction. The echoes of the field over the covered area are then measured by the same group of elements or by a smaller group of elements. In the example shown in FIG. 1, the ultrasound field is transmitted in a direction perpendicular to the axis of alignment of the elements 102, which also locally corresponds to the plane of the skin 103 on which the probe 101 is positioned.

Figure 3A:
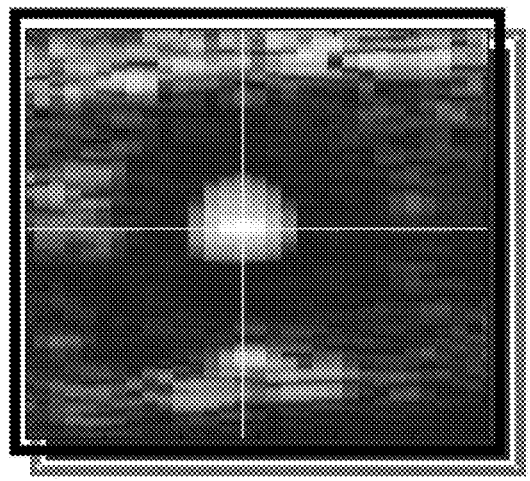
FIG. 3a shows an example of an ultrasound image obtained in order to characterise a blood vessel.

FIG. 3a shows an example of a 2D image obtained by carrying out several successive acquisitions, each time shifting the transmission centre of the ultrasound field relative to the covered area.

Figure 3B:
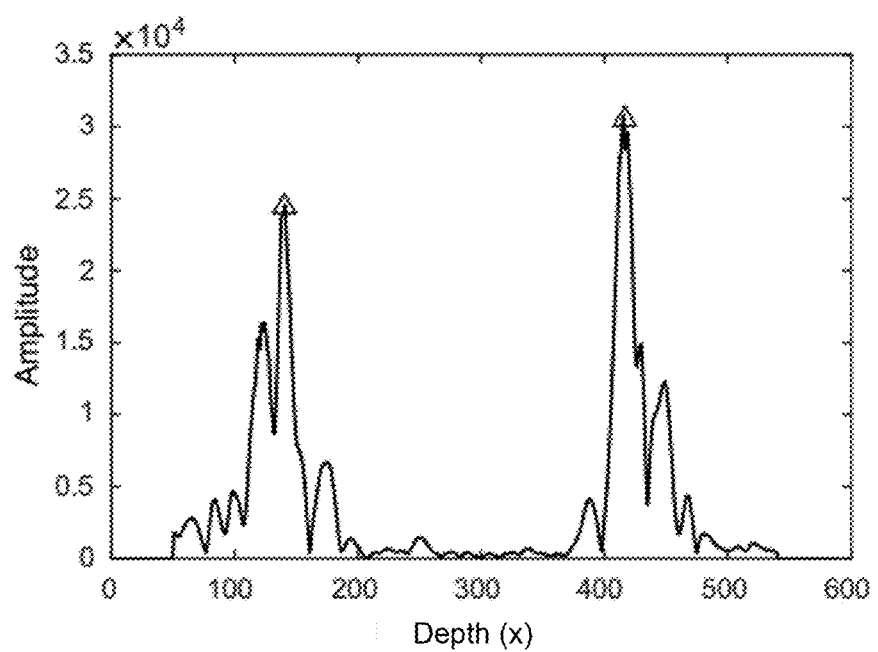

FIG. 3b shows a column of the 2D image of FIG. 3a that corresponds to a signal measured for an acquisition corresponding to a position of the probe that is in line with the centre of the vessel to be imaged.

Indeed, the 2D image of FIG. 3a corresponds to a matrix, each column of which is one of the ultrasound signals acquired by the probe for a given position of the transmitted field relative to the imaged zone.

In FIG. 3b, two triangles have been used to identify two extrema corresponding to the echoes of the ultrasound field on the distal and proximal walls of the blood vessel (in this case a radial artery).

These two points correspond to points of interest within the context of determining the diameter of the vessel. Indeed, based on the measurement of the times-of-flight of these two extrema, it is possible to deduce the positions of the two points therefrom and then the diameter, assuming that the signal corresponds to a path that passes through the centre of the artery. The internal diameter of the vessel is equal to $D=0.5C \cdot (t_2-t_1)$, where $t_2$, $t_1$ are the abscissae of the two extrema (time-of-flight) and C is the propagation speed of the ultrasound wave in the medium, in this case the blood.

However, the precision of the measurement of the time-of-flight of a point of interest depends on the size of the active window of the probe on transmission, as will now be explained.

Figure 4A:
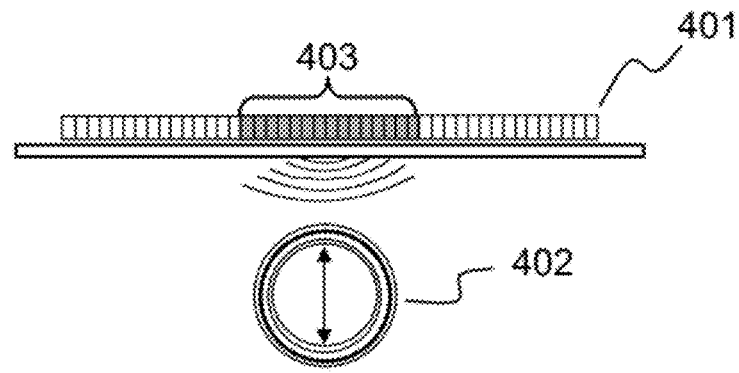
FIG. 4a shows a diagram of an ultrasound probe in a first size configuration for a reception active window.
Figure 4B:
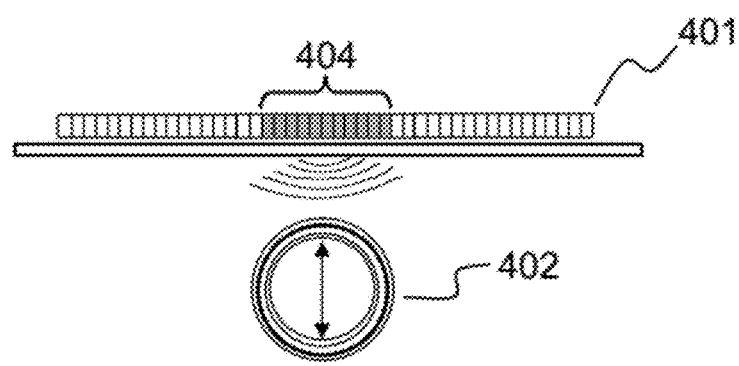
FIG. 4b shows a diagram of an ultrasound probe in a second size configuration for a reception active window.
Figure 4C:
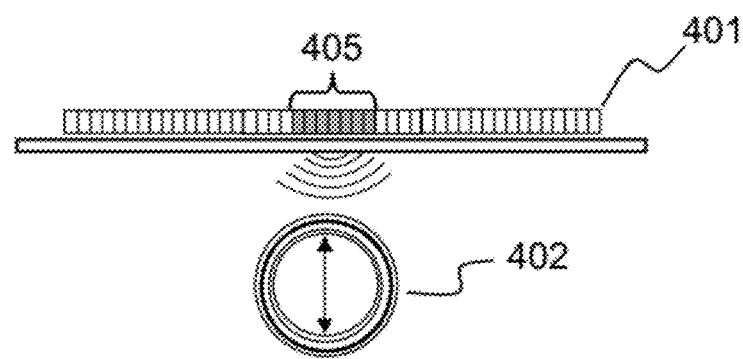
FIG. 4c shows a diagram of an ultrasound probe in a third size configuration for a reception active window.

FIGS. 4a, 4b and 4c show three different acquisition configurations for the same ultrasound probe 401 disposed in line with a radial artery 402.

For the first configuration shown in FIG. 4a, the number of transmission and reception active elements 403 is equal to 16. In other words, the ultrasound field is generated based on the 16 central elements of the probe and is also measured by these 16 elements. This acquisition allows a first measurement to be obtained of the signal shown in FIG. 3b.

The second configuration schematically shown in FIG. 4b shows a situation where the number of reception active elements 404 is equal to 12. In this configuration, the number of transmission active elements also can be taken to be equal to 12 or can be taken to be equal to 16, i.e., the maximum number of transmission active elements that is predefined according to the intended application.

The third configuration shown in FIG. 4c shows yet another situation where the number of reception active elements 405 is equal to 8. The number of transmission active elements is equal to 8 or 16.

In general, FIGS. 4a, 4b and 4c show that it is possible to carry out the same measurement based on a variable active window size. The larger the window, the higher the signal-to-noise ratio, but the lower the measurement precision of the echo at a given point. Conversely, a minimum active window size is required in order to obtain a measurement with a usable signal-to-noise ratio.

Figure 2:
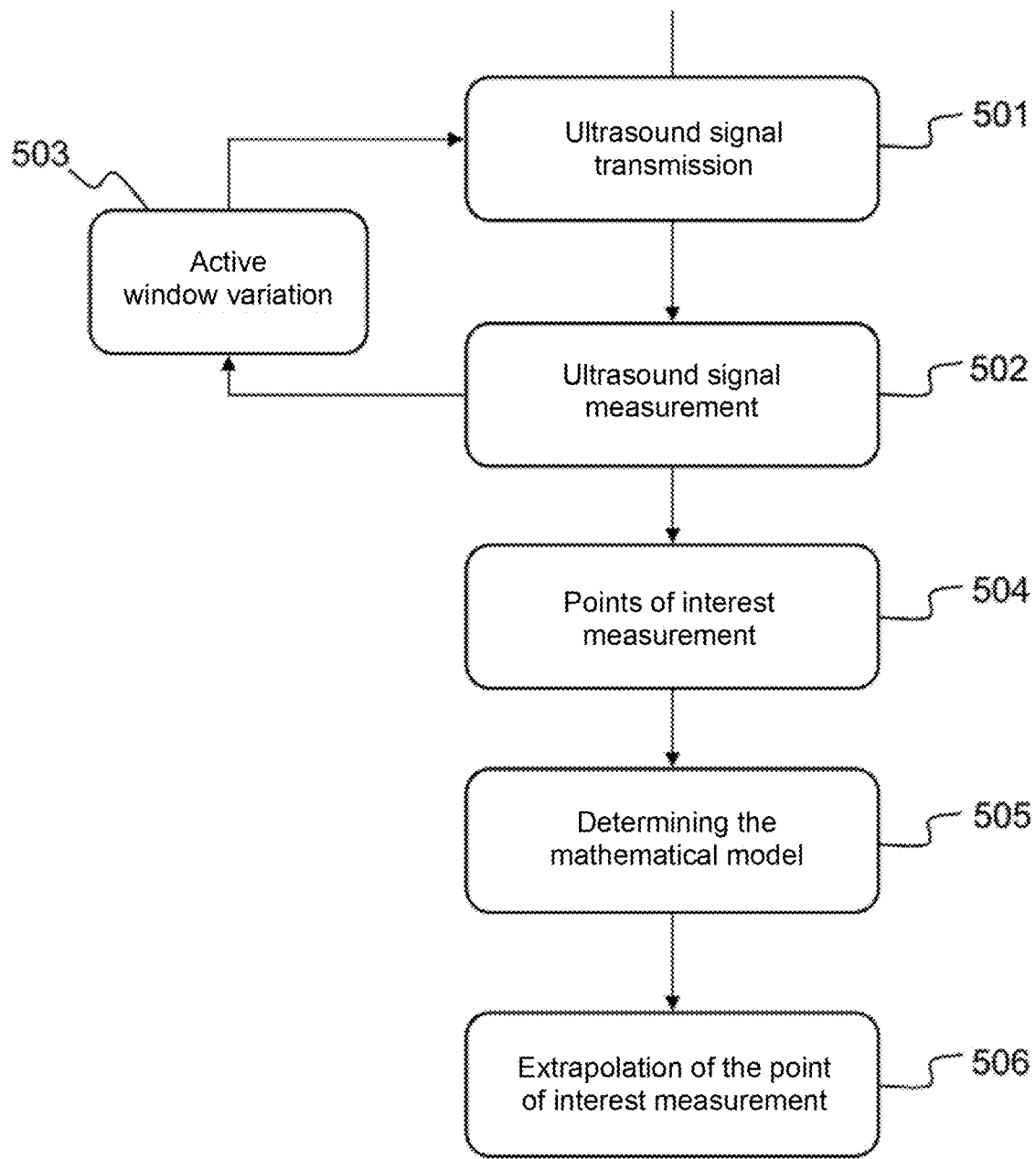
FIG. 2 shows a flow chart of the steps of a method for measuring an ultrasound signal according to one embodiment of the invention.

With reference to FIG. 2, the measurement method according to the invention begins with steps 201, 202 and 203, which involve carrying out several successive acquisitions of the same ultrasound signal (for the same position of the probe relative to the object to be imaged), by varying the size of the active window for each iteration.

For example, in the case of a multi-element transducer, the number of reception active elements can be reduced for each iteration compared with the maximum number of elements used to generate the ultrasound beam. For each iteration, the number of transmission active elements can be kept constant or the group of transmission active elements can be taken to be equal to the group of reception active elements.

For example, for each iteration, the number of reception active elements can be reduced by a factor of 2.

According to another embodiment, if the ultrasound probe is manufactured using technology that allows the aperture of the ultrasound field to be varied with a single element, then the variation in the number of reception active elements is replaced by a variation in the aperture field for each iteration.

On completion of all the iterations of steps 201, 202, 203, N measurements of the same ultrasound signal are obtained, where N is the completed number of acquisitions.

One or more points of interest is/are then identified on the acquired ultrasound signal. For example, in the case of the signal of FIG. 5, two points of interest 501, 502 are identified that correspond to echoes of the signal on the distal and proximal internal walls of the blood vessel.

Figure 5:
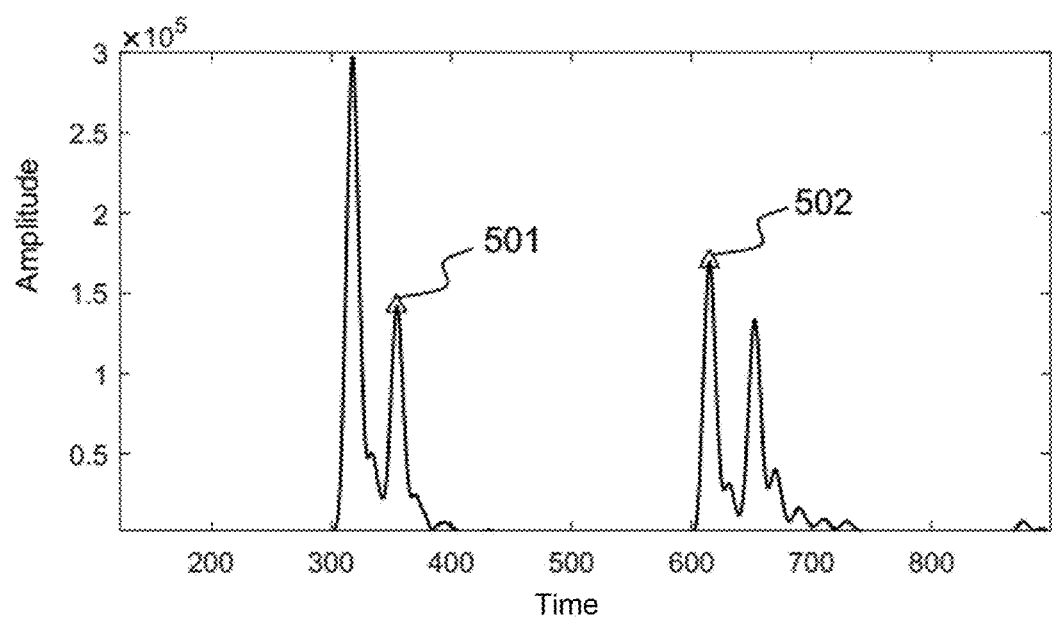
FIG. 5 shows an example of an ultrasound signal obtained in a particular size configuration for an active window.

For each of these two points, the intention is to precisely determine the associated time-of-flight or depth (with the two quantities being connected by the speed of propagation of the ultrasound wave in the medium between the probe and the artery), which is shown on the abscissa of the diagram in FIG. 5.

Figure 6A:
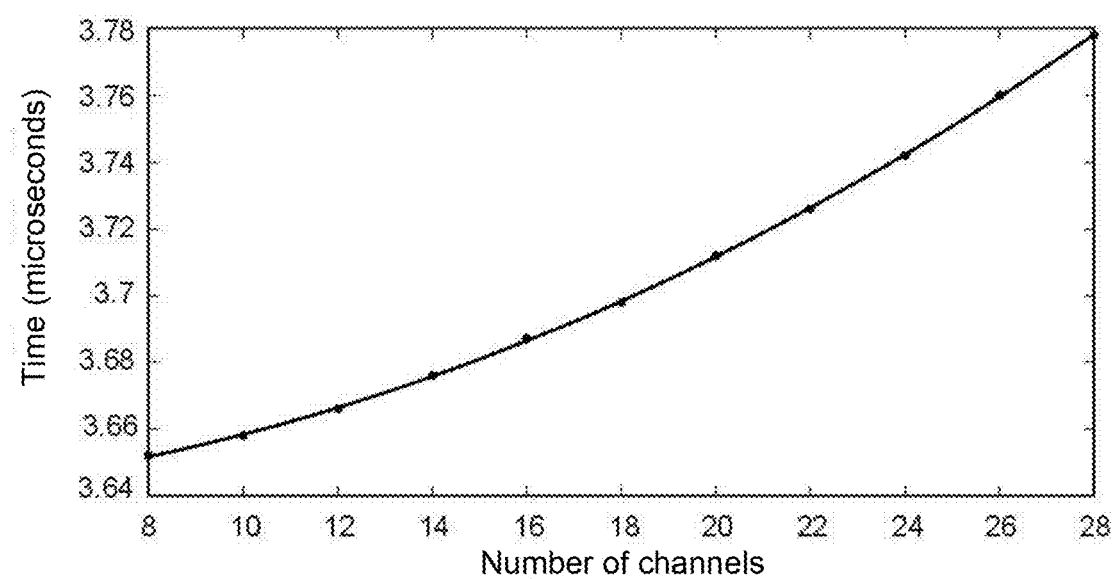
FIG. 6a shows a diagram providing the variation in the time-of-flight of a first point of interest in the ultrasound signal as a function of the size of the active window.
Figure 6B:
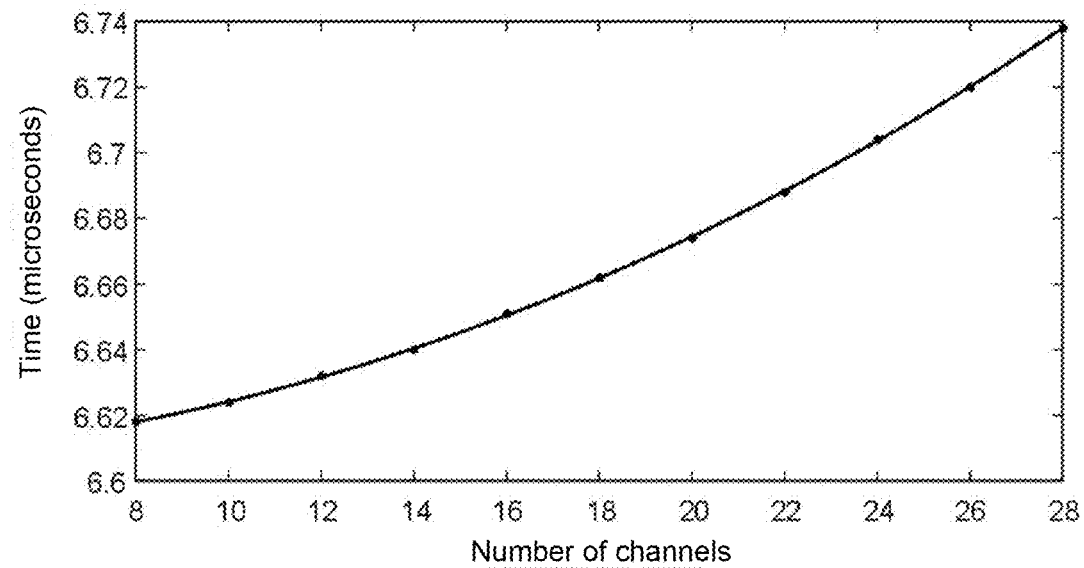
FIG. 6b shows a diagram providing the variation in the time-of-flight of a second point of interest of the ultrasound signal as a function of the size of the active window.

For each considered point of interest, its abscissa is recorded (expressed as time-of-flight or distance) and the diagrams shown in FIGS. 6a and 6b are drawn (in step 204), which show the evolution of these measurements as a function of the number of reception active elements, also called the number of channels in FIGS. 6a and 6b. FIG. 6a corresponds to the position of the echo of the signal on the proximal wall and FIG. 6b corresponds to the position of the echo of the signal on the distal wall. In the examples shown, the number of channels varies from 8 to 28, but this example is by no means limiting. The ordinate shows the time-of-flight for each measurement.

In step 205, a mathematical optimisation is then used to determine a digital model of the evolution of the time-of-flight variation curves as a function of the number of channels for each point of interest.

This mathematical model is determined, for example, by a model in the form of a second-degree polynomial function or of any other suitable digital model. It can be defined by interpolating the measured points of the curve. This interpolation can be carried out using a mixture of Gaussian functions or can be learned by a trained neural network model or by any other suitable digital optimisation algorithm.

Figure 6C:
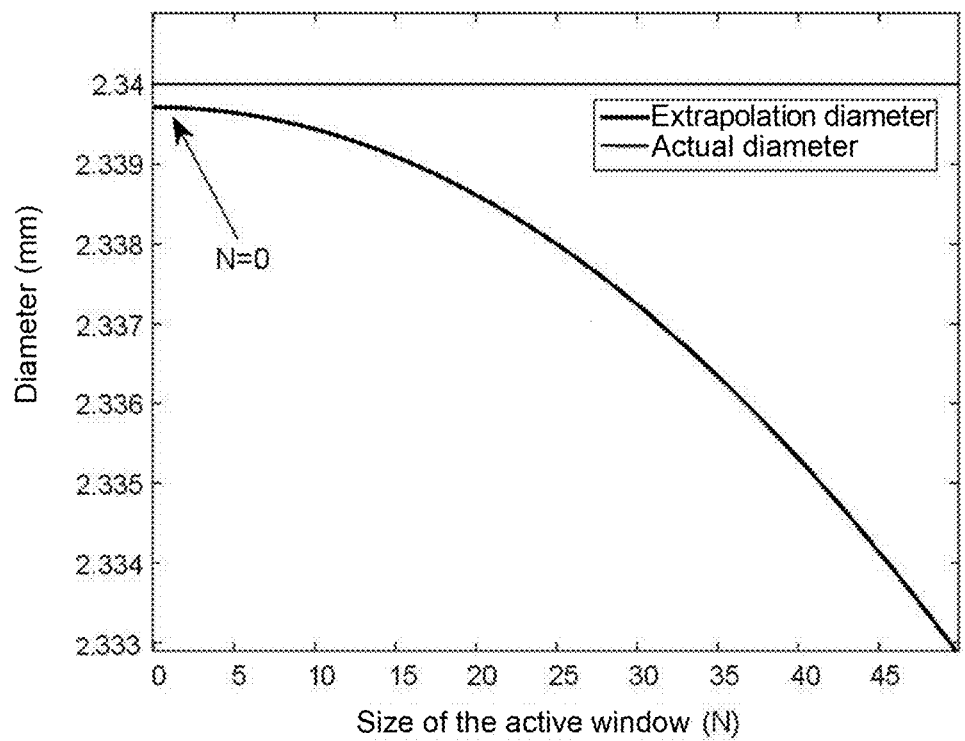
FIG. 6c shows a diagram of a mathematical model of the variation in the estimated diameter of a blood vessel based on the times-of-flight of the two points of interest measured in FIGS. 6a and 6b.

FIG. 6c shows an example of such a digital model determined for the difference between the two curves in FIGS. 6a and 6b, which, in the intended application case, corresponds to the diameter of the blood vessel.

The mathematical model can be determined for each curve associated with each point of interest or for the final quantity that is intended to be determined based on several points of interest, in this case the difference between the two times-of-flight.

Finally, in step 206, the mathematical model that is obtained is extrapolated in order to determine an asymptotic value for a number of channels tending towards 0. Indeed, this value corresponds to the most precise measurement in terms of resolution, and determining it by extrapolating a model avoids experiencing the problem of a low signal-to-noise ratio inherent in a measurement carried out with a very small active window.

For example, the diameter of the vessel is determined using the following relationship:

$D = 0.5(t_{distal}(0) - t_{proximal}(0)) \cdot C$, where C designates the speed of propagation of the ultrasound wave in the medium that is traversed, $t_{distal}(0)$ and $t_{proximal}(0)$ are the extrapolated values for a number of channels tending towards 0 for the evolution models of the times-of-flight associated with the points of interest corresponding to the echoes of the ultrasound field on the distal wall and on the proximal wall of the vessel, respectively.

In general, the invention can be similarly applied in order to improve the precision of a time-of-flight measurement of a point of interest corresponding to the echo of an ultrasound field on the surface of an object to be imaged.

REFERENCES

[1] J. H. Gagan et al., "Automated Segmentation of Common Carotid Artery in Ultrasound Images", in IEEE Access, vol. 10, pp. 58419-58430, 2022.
[2] "System A feasibility study of a PMUT-based wearable sensor for the automatic monitoring of carotid artery parameters", 2021 IEEE International Ultrasonics Symposium (IUS).

The invention claimed is:

1. A method for measuring features of an object to be imaged using an ultrasound probe, the method comprising the following steps of:
    executing, with the ultrasound probe, two or more iterations of the following steps of:
        i. transmitting, with the ultrasound probe, an ultrasound field having an aperture with a given size;
        ii. receiving, with the ultrasound probe, an echo of the ultrasound field following reflection on a zone of interest of an object to be imaged;
        iii. modifying, for each new iteration, the size of the aperture of the ultrasound field;
    recording, for at least one point of interest in the zone of interest, an associated time-of-flight on the received echo;
    determining, a variation model of recorded times-of-flight as a function of the size of the aperture of the ultrasound field;
    extrapolating the time-of-flight of the at least one point of interest for a value of an aperture size tending towards 0 based on said model.

2. The method for measuring features of an object according to claim 1, wherein the ultrasound probe comprises a plurality of elements and the variation in the size of the aperture of the ultrasound field is obtained by varying a number of the plurality of elements that are active in reception.

3. The method for measuring features of an object according to claim 2, wherein the number of the plurality of elements that are active in reception is a multiple of two.

4. The method for measuring features of an object according to claim 2, wherein a number of the plurality of elements that are active in transmission is equal to the number of the plurality of elements that are active in reception or to a maximum number of elements included in the probe.

5. The method for measuring features of an object according to claim 1, wherein the object to be imaged is a blood vessel and the at least one point of interest is a point on a wall of the blood vessel.

6. The method for measuring features of an object according to claim 5, wherein the at least one point of interest comprises two points of interest corresponding to a first point on the distal wall of the blood vessel and a second point on the proximal wall of the blood vessel, diametrically opposite the first point, and the method further comprises estimating the diameter of the blood vessel based on the extrapolated times-of-flight of the two points.

7. An ultrasound imaging device comprising the ultrasound probe and a processing unit configured to carry out the steps of the method using the ultrasound probe according to claim 1.

* * * * *